United States Patent [19]

Hesse

[11] Patent Number: Plant 6,777

[45] Date of Patent: May 2, 1989

[54] CHRYSANTHEMUM PLANT NAMED BOURBON STREET

[75] Inventor: Peter S. Hesse, Bradenton, Fla.

[73] Assignee: Ball Seed Company, West Chicago, Ill.

[21] Appl. No.: 139,765

[22] Filed: Dec. 30, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Bourbon Street having golden bronze ray florets, disc florets which are greyed orange with a dark eye in the center, anemone flower form, 6 week flower response; compact, semi-upright habit, free branching and flower, and suitability for garden mum production.

1 Drawing Sheet

The present invention comprises a new and distinct cultivar of *Chrysanthemum morifolium,* hereinafter referred to by the cultivar name Bourbon Street.

Bourbon Street is a product of a planned breeding program which had the objective of creating new Chrysanthemum cultivars having compact growth habit, early flowering, anemone flower form, and suitability for production as a garden mum. Such traits in combination were not present or needed improvement in previously available commercial cultivars.

Bourbon Street was originated from a hybridization made by applicant in a controlled breeding program in Parrish, Fla. in 1984. The female parent was Viva. The male parent of Bourbon Street was Volunteer. Bourbon Street was discovered and selected as one flowering plant within the progeny of the stated parentage by applicant in November 1984 in a controlled environment in Parrish, Fla.

The first act of asexual reproduction of Bourbon Street was accomplished when vegetative cuttings were taken from the initial selection in March 1985 in a controlled environment in Parrish, Fla. by a technician working under formulations established and supervised by applicant. Horticultural examination of selected units initiated in September 1985 has demonstrated that the combination of characteristics as herein disclosed for Bourbon Street are firmly fixed and are retained through successive generations of asexual reproduction.

The following traits have been repeatedly observed and are determined to be basic characteristics of Bourbon Street, which in combination distinguish this Chrysanthemum as a new and distinct cultivar:

1. Six week flower response.
2. Golden bronze ray florets.
3. Immature disc displays a round dark violet blue area or eye in the center. This eye and the surrounding ring of disc florets fade to a light greyed orange color when the flower is fully mature. When grown under very high temperatures, the eye may be absent altogether.
4. Anemone flower form.
5. Ray florets are flat and are up to 2.5 cm long and 9 mm wide.
6. Disc florets are funnelform and up to 12 mm long.
7. Total flower diameter reaches 5.5 cm.
8. Compact, semi-upright habit.
9. Freely branching and flowering.

10. Suitable for use as a garden mum for production in 4½" to 1 gallon containers.

Bourbon Street has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

Of the many commercial cultivars known to the present inventor, the most similar in comparison to Bourbon Street in Carmella. In comparison to Carmella, Bourbon Street has a more compact growth habit, 2 week earlier flower response, and displays a dark eye in its immature disc. The bronze color and flower form of Bourbon Street are similar to those same characteristics of Carmella.

The accompanying photographic drawing shows typical inflorescence and foliage characteristics of Bourbon Street. The photograph is in black and white with several flowers being displayed in color which depicts the true ray and floret colors as noted below.

In the following description, color references are made to The Royal Horticultural Society Colour Chart. The color values were determined between 2:00 and 2:30 p.m. on Oct. 21, 1987 under fluorescent light at Parrish, Fla.

Classification:

*Botanical.*—*Chrysanthemum morifolium,* cv. Bourbon Street.

*Commercial.*—Anemone garden mum.

INFLORESCENCE

A. Capitulum:

*Form.*—Flat.

*Type.*—Anemone.

*Diameter across face.*—Up to 5.4 cm.

B. Corolla of ray florets:

*Color (general tonality from a distance of three meters).*—Bronze.

*Color (upper surface).*—165D.

*Color (lower surface).*—164D.

C. Corolla of disc florets:

*Color (immature).*—163 A, with dark violet blue eye in center, approximately 95A.

*Color (mature).*—Both violet blue eye in center and the surrounding ring fade eventually to approximately 163D.

D. Reproductive organs:

*Androecium.*—Present in disc florets only.

*Gynoecium.*—Present in both disc and ray florets.

PLANT

A. General appearance:

*Height.*—20 cm when grown in the ground, given no long days and one pinch. Height will vary depending upon growing conditions.

B. Foliage:

*Color (upper surface).*—147A.

*Color (lower surface).*—147B.

*Shape.*—Ovate, deeply lobed with serrate margins.

I claim:

1. A new and distinct cultivar of Chrysanthemum plant named Bourbon Street, as illustrated and described, and parts thereof.

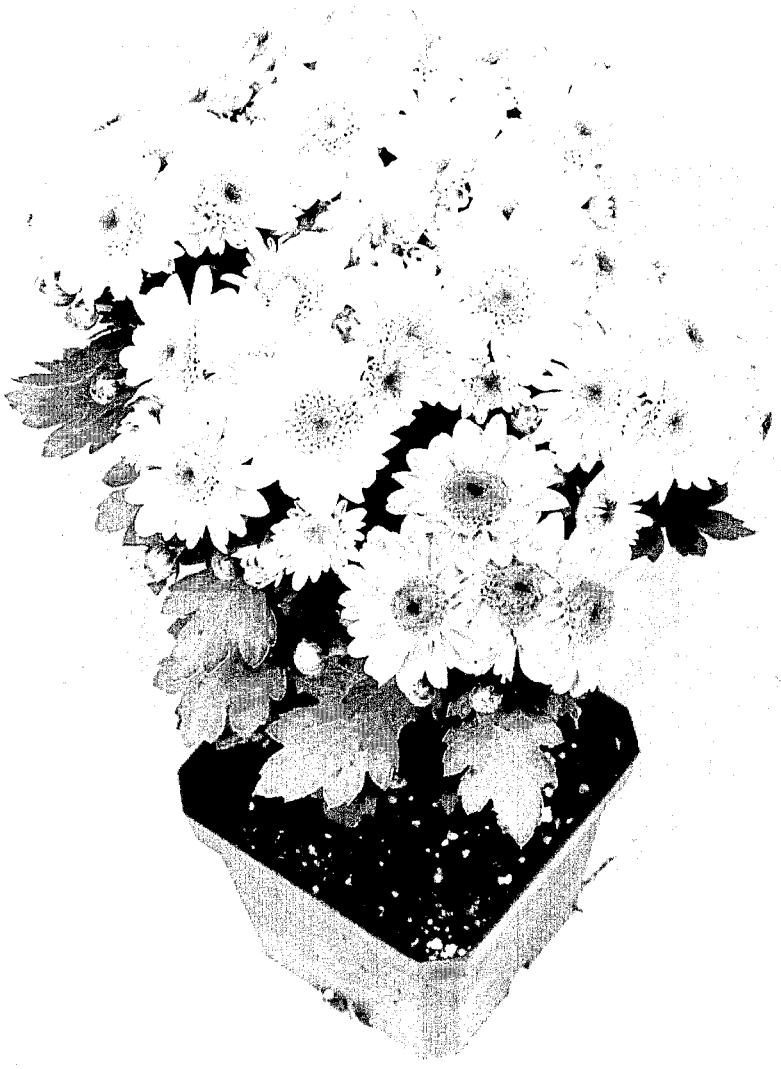

* * * * *